US011247959B2

(12) United States Patent
Ni et al.

(10) Patent No.: US 11,247,959 B2
(45) Date of Patent: Feb. 15, 2022

(54) METHOD FOR DIRECTLY PREPARING DIMETHYL ETHER BY SYNTHESIS GAS

(71) Applicant: Dalian Institute of Chemical Physics, Chinese Academy of Sciences, Dalian (CN)

(72) Inventors: Youming Ni, Dalian (CN); Wenliang Zhu, Dalian (CN); Zhongmin Liu, Dalian (CN); Yong Liu, Dalian (CN); Hongchao Liu, Dalian (CN); Xiangang Ma, Dalian (CN); Shiping Liu, Dalian (CN)

(73) Assignee: Dalian Institute of Chemical Physics, Chinese Academy of Sciences, Dalian (CN)

( * ) Notice: Subject to any disclaimer, the term of this patent is extended or adjusted under 35 U.S.C. 154(b) by 0 days.

(21) Appl. No.: 17/054,894

(22) PCT Filed: Aug. 1, 2018

(86) PCT No.: PCT/CN2018/098069
§ 371 (c)(1),
(2) Date: Nov. 12, 2020

(87) PCT Pub. No.: WO2019/218490
PCT Pub. Date: Nov. 21, 2019

(65) Prior Publication Data
US 2021/0246093 A1 Aug. 12, 2021

(30) Foreign Application Priority Data
May 17, 2018 (CN) .......................... 201810473642.1

(51) Int. Cl.
*C07C 41/01* (2006.01)
*B01J 8/06* (2006.01)
(Continued)

(52) U.S. Cl.
CPC ................ *C07C 41/01* (2013.01); *B01J 8/06* (2013.01); *B01J 21/02* (2013.01); *B01J 37/009* (2013.01);
(Continued)

(58) Field of Classification Search
CPC .......... C07C 41/01; C07C 41/09; B01J 21/02; B01J 21/04; B01J 21/06; B01J 23/005; B01J 37/0213
See application file for complete search history.

(56) References Cited

U.S. PATENT DOCUMENTS

2007/0142482 A1* 6/2007 Jung ...................... B01J 23/002
518/726
2013/0210940 A1* 8/2013 Schafer .................... B01J 31/04
518/713
2013/0211147 A1 8/2013 Cheiky et al.

FOREIGN PATENT DOCUMENTS

CN 104114274 A 10/2014
CN 105148912 A 12/2015
(Continued)

OTHER PUBLICATIONS

Alkeos C. Sofianos et al., Conversion of Synthesis Gas to Dimethyl Ether over Bifunctional Catalytic Systems, Industrial & Engineering Chemistry Research, 1991, 2372-2378, 30, Washington Dc, US.

*Primary Examiner* — Jafar F Parsa
(74) *Attorney, Agent, or Firm* — Edwin A. Sisson, Attorney at Law, LLC; Jeffrey J. Banyas

(57) ABSTRACT

Provided is a method for directly preparing dimethyl ether by synthesis gas, the method comprises: the synthesis gas is passed through a reaction zone carrying a catalyst, and reacted under the reaction conditions sufficient to convert at least a portion of the raw materials to obtain the reaction effluent comprising dimethyl ether; and the dimethyl ether is separated from the reaction effluent, wherein the catalyst is
(Continued)

zinc aluminum spinel oxide. In the present invention, only one zinc aluminum spinel oxide catalyst is used, which can make the synthesis gas to highly selectively form dimethyl ether, the catalyst has good stability and can be regenerated. The method of the present invention realizes the production of dimethyl ether in one step by the synthesis gas, and reduces the large energy consumption problem caused by step-by-step production.

10 Claims, 2 Drawing Sheets

(51) Int. Cl.
  *B01J 21/02*  (2006.01)
  *B01J 37/00*  (2006.01)
  *B01J 37/02*  (2006.01)
  *B01J 37/04*  (2006.01)
  *B01J 37/06*  (2006.01)
  *B01J 37/08*  (2006.01)
(52) U.S. Cl.
  CPC ....... *B01J 37/0063* (2013.01); *B01J 37/0213* (2013.01); *B01J 37/04* (2013.01); *B01J 37/06* (2013.01); *B01J 37/082* (2013.01)

(56) References Cited

FOREIGN PATENT DOCUMENTS

| EP | 0409086 A1 | 1/1991 |
| EP | 2814601 A1 | 12/2014 |

* cited by examiner

METHOD FOR DIRECTLY PREPARING DIMETHYL ETHER BY SYNTHESIS GAS

PRIORITIES AND CROSS REFERENCES

This Application claims priority from International Application No. PCT/CN2018/098069 filed on 1 Aug. 2018 and Chinese Application No. 201810473642.1 filed on 17 May 2018 the teachings of each of which are incorporated by reference herein in their entirety.

TECHNICAL FIELD

The present invention refers to a method for directly preparing dimethyl ether from syngas.

BACKGROUND

Dimethyl ether ($CH_3OCH_3$, DME) is a non-toxic, harmless and non-corrosive chemical. Due to its high cetane number, no nitrogen and sulfur included, and good compatibility with diesel and the like benefits, dimethyl ether is a very potential and clean diesel additive. The dimethyl ether has very similar physical and chemical properties to liquefied petroleum gas, and is widely used in the field of household fuels. In recent years, the "coal-to-ethanol" technology has always been a research hotspot in the field of "coal chemical industry", such as the technology of "conversion of coal into dimethyl ether, and further carbonylation and hydrogenation to produce anhydrous ethanol". Thus, dimethyl ether will be widely used in the technology for synthetizing fuel ethanol in the future. At present, dimethyl ether is mainly industrially produced through the dehydration reaction of methanol with solid acidic catalysts. It is known that methanol is mainly synthesized from syngas with a copper zinc aluminum ($CuZnAlO_x$) methanol synthesis catalyst. In order to save fixed investment and reduce energy consumption, people hope that the syngas can be directly converted into dimethyl ether. Among a large number of reports about the direct preparation of dimethyl ether from syngas, the most researches are based on $CuZnAlO_x$/solid acidic (acidic molecular sieve or $\gamma$-$Al_2O_3$) composite catalyst. Methanol synthesis catalysts are generally used below 250° C., but the solid acidic catalyst for methanol dehydration reaction needs to be used higher than 250° C. to exert good performance. Thus, the general operating temperature of the composite catalysts is in a range from 250° C. to 300° C. Under high-temperature reaction conditions, the stability of the composite catalyst becomes poor, and $CuZnAlO_x$ cannot be regenerated, which have resulted in that the direct synthesis of dimethyl ether from syngas has not been industrialized so far.

SUMMARY

In order to overcome the problems in the prior art, the inventors of the present application conducted diligent research. As a result, it was found that zinc-aluminum spinel oxide is very suitable as a catalyst for directly preparing dimethyl ether from syngas. With this catalyst, the method for directly preparing dimethyl ether from syngas can make syngas be converted into dimethyl ether with high selectivity. This catalyst not only is stable but also can be regenerated, thereby reducing large energy consumption caused by stepwise production. The inventors completed the present invention based on the above findings.

Therefore, one object of the present invention is to provide a method for directly preparing dimethyl ether from syngas comprising:
passing syngas through a reaction zone loaded with catalyst, and reacting under a reaction condition sufficient to convert at least part of the syngas as raw materials to obtain a reaction effluent containing dimethyl ether; and separating dimethyl ether from the reaction effluent;
wherein, the catalyst is zinc-aluminum spinel oxide.

In one embodiment, the reaction zone contains one fixed bed reactor, or multiple fixed bed reactors in series and/or in parallel.

In one embodiment, the reaction condition comprises: a reaction temperature ranging from 300 to 450° C., a reaction pressure ranging from 0.5 to 10.0 MPa, a molar ratio of hydrogen to carbon monoxide in the syngas ranging from 1:9 to 9:1, and the volume hourly space velocity of syngas under standard conditions ranging from 1,000 to 20,00010.

DESCRIPTION OF THE PREFERRED EMBODIMENTS

The present invention provides a method for directly preparing dimethyl ether from syngas comprising:
passing syngas through a reaction zone loaded with catalyst, and reacting under a reaction condition sufficient to convert at least part of raw materials to obtain a reaction effluent containing dimethyl ether; and
separating the dimethyl ether from the reaction effluent, wherein, the catalyst is zinc-aluminum spinel oxide.
Catalyst for Preparing Dimethyl Ether As mentioned above, the catalyst used in the method of the present invention is zinc-aluminum spinel oxide.

The molar ratio of Zn/Al in the zinc-aluminum spinel oxide of the present invention is any ratio, preferably Zn/Al=1:9 to 1:1, for example, Zn/Al=1:1, 1:2, 1:4.5 or 1:9.

In some embodiments, the size of zinc aluminum spinel crystal in the zinc-aluminum spinel oxide is less than or equal to 30 nm.

In some embodiments, the zinc-aluminum spinel oxide further comprises at least one other element selected from chromium, zirconium, copper, manganese, indium, gallium, and silicon. The at least one other element is added to the zinc-aluminum spinel oxide by impregnating and/or co-precipitating a salt solution of the at least one other element. Preferably, the mass fraction of the at least other element in the zinc-aluminum spinel oxide is less than or equal to 10%, for example, 1%, 3%, 5%, 7%, 9% or 10%.

In one embodiment, the zinc-aluminum spinel oxide is prepared by a precipitation-calcination method. For example, the zinc-aluminum spinel oxide is prepared by following steps: formulating a zinc salt and an aluminum salt into a mixed metal salt aqueous solution; contacting the mixed metal salt aqueous solution with a precipitant aqueous solution so as to make the metal ions in the mixed metal salt aqueous solution be co-precipitated followed by aging; washing the obtained precipitate followed by drying and then calcining to obtain the zinc-aluminum spinel oxide. Examples of the precipitant include, but are not limited to, sodium carbonate, potassium carbonate, ammonium carbonate, sodium bicarbonate, potassium bicarbonate, ammonium bicarbonate, aqueous ammonia, sodium hydroxide, potassium hydroxide, and mixtures thereof.

In one embodiment, the temperature during the coprecipitation ranges from 20° C. to 95° C., the pH during the coprecipitation ranges from 7.0 to 9.0, the aging time is not less than 1 hour, and the calcining temperature ranges from 450° C. to 800° C.

In a specific embodiment, the zinc-aluminum spinel oxide is prepared as follows: dissolving any ratio of zinc salt to aluminum salt in deionized water to form a mixed metal salt aqueous solution, wherein the concentration of the mixed metal salt aqueous solution can be any concentration where the mixed metal salt is completely dissolved in deionized water at room temperature; dissolving the precipitant in deionized water to prepare a precipitant aqueous solution, wherein the concentration of the precipitant aqueous solution can be any concentration where the precipitant is completely dissolved in the deionized water at room temperature; contacting the mixed metal salt aqueous solution with the precipitant aqueous solution so as to make the metal ions in the mixed metal salt aqueous solution be co-precipitated at a temperature ranging from 20 to 95° C., wherein, the pH is controlled between 7.0 and 9.0 by controlling the flow rate of the mixed metal salt aqueous solution and the precipitant aqueous solution during the coprecipitation; after the coprecipitation is completed, performing aging step at a temperature ranging from 20 to 95° C. for a time ranging from 1 to 24 hours, followed by centrifugal separation, washing with deionized water, drying at 100° C. for 24 hours, and finally calcining at a temperature ranging from 450 to 800° C. for a time ranging from 2 to 10 hours to obtain the zinc-aluminum spinel oxide.

In the present invention, there are no special limitations about the types of the zinc salt, aluminum salt and the salt of at least one other element, as long as they are water-soluble. For example, any of them has a water solubility greater than 1 g/L at 25° C. Examples of the zinc salt, aluminum salt, and the salt of at least one other element include, but are not limited to, hydrochloride, sulfate and nitrate.

In the method of the present invention, there are no special limitations about the contacting manners of the mixed metal salt aqueous solution with the precipitant aqueous solution. In a specific embodiment, the contact can be achieved by co-current feeding, forward feeding or reverse feeding.

Method for Preparing Dimethyl Ether from Syngas As mentioned above, the syngas contacts with the catalyst in the reaction zone under a reaction condition sufficient to convert at least part of the syngas as raw materials to obtain a reaction effluent containing dimethyl ether.

Without wishing to be limited to any specific theory, it is believed that the direct synthesis of dimethyl ether from syngas involves a series of reaction processes, such as:
1) Methanol Synthesis Reaction:

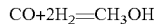
CO+2H$_2$=CH$_3$OH

2) Reaction of Methanol Dehydration to Dimethyl Ether:

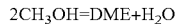
2CH$_3$OH=DME+H$_2$O

3) Water-Gas Shift Reaction:

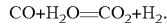
CO+H$_2$O=CO$_2$+H$_2$.

The term "syngas" used herein refers to a mixed gas of hydrogen and carbon monoxide. In the syngas as raw materials, the molar ratio of hydrogen to carbon monoxide may range from 1:9 to 9:1, preferably range from 1:9 to 1:1.

Since the main side reaction in the direct synthesis of dimethyl ether from syngas is the water-gas shift reaction which is a typical equilibrium reaction, the addition of carbon dioxide is beneficial to inhibit the water-gas shift reaction and improve the utilization efficiency of carbon monoxide. Therefore, the syngas in the method of the present invention can also comprise carbon dioxide. The molar concentration of carbon dioxide in the syngas ranges from 1.0% to 20.0%. For example, the molar concentration of carbon dioxide in the syngas can be 1%, 3%, 5%, 8%, 10%, 13%, 15%, 17% or 20%.

In the method of the present invention, the reaction zone may contain one or more fixed bed reactors. The fixed bed reactor(s) can be operated in continuous mode. When many fixed bed reactors are employed, the reactors can be connected in series, in parallel or in a combination of in series and in parallel.

In one embodiment, the reaction condition comprises: a reaction temperature ranging from 300 to 450° C., a reaction pressure ranging from 0.5 to 10.0 MPa, a molar ratio of hydrogen to carbon monoxide in the syngas ranging from 1:9 to 9:1, and the volume hourly space velocity of syngas under standard conditions ranging from 1,000 to 20,000 h$^{-1}$.

In one preferred embodiment, the reaction condition comprises: a reaction temperature ranging from 310 to 360° C., a reaction pressure ranging from 1.0 to 4.0 MPa, a molar ratio of hydrogen to carbon monoxide in the syngas ranging from 3:1 to 6:1, and the volume hourly space velocity of syngas under standard conditions ranging from 3000 to 8000 h$^{-1}$.

Separation of the Reaction Effluent

In the method of the present invention, the separation of the dimethyl ether from the reaction effluent containing dimethyl ether can be carried out according to a method known per se.

The advantageous effects achieved by the present invention comprises:
1) In the present invention, only the zinc-aluminum spinel oxide catalyst is used, by which can dimethyl ether can be produced from the syngas with high selectivity, and the catalyst possesses good stability and can be regenerated.
2) By the addition of carbon dioxide, the water-gas shift reaction can be effectively inhibited, and the carbon monoxide utilization efficiency is high.
3) The method of the present invention realizes the production of dimethyl ether from the syngas in one step, thereby reducing large energy consumption caused by stepwise production.

DETAILED DESCRIPTION

The present invention is described in detail by the following examples, but the invention is not limited to these examples.

Unless otherwise indicated, raw materials employed in the examples of the present application are commercially purchased.

In the examples, automatic analysis is performed by an Agilent 7890 Gas Chromatograph with a gas autosampler, a TCD detector connected to a TDX-1 packed column, and an FID detector connected to a PLOT-Q capillary column.

In the examples, conversion efficiency and selectivity are calculated based on the molar number of carbon:

Conversion efficiency of carbon monoxide=[(the molar number of carbon monoxide in the feeding raw materials)−(the molar number of carbon monoxide in the product)]÷(the molar number of carbon monoxide in the feeding raw materials)×100%

Dimethyl ether selectivity=(the molar number of carbon of dimethyl ether in the product)÷(the sum of the molar number of carbon in all hydrocarbons, methanol, and dimethyl ether in the product)×100%

Methanol ether selectivity=(the molar number of carbon of methanol in the product)÷(the sum of the molar number of carbon in all hydrocarbons, methanol, and dimethyl ether in the product)×100%

Hydrocarbons selectivity=(the molar number of carbon of hydrocarbons in the product)÷(the sum of the molar number of carbon in all hydrocarbons, methanol, and dimethyl ether in the product)×100%

Carbon dioxide selectivity=(the molar number of carbon dioxide produced in the reaction)÷(the molar number of carbon monoxide converted)×100%.

Preparation of Zinc-Aluminum Spinel Oxide

Example 1

Figure 1:
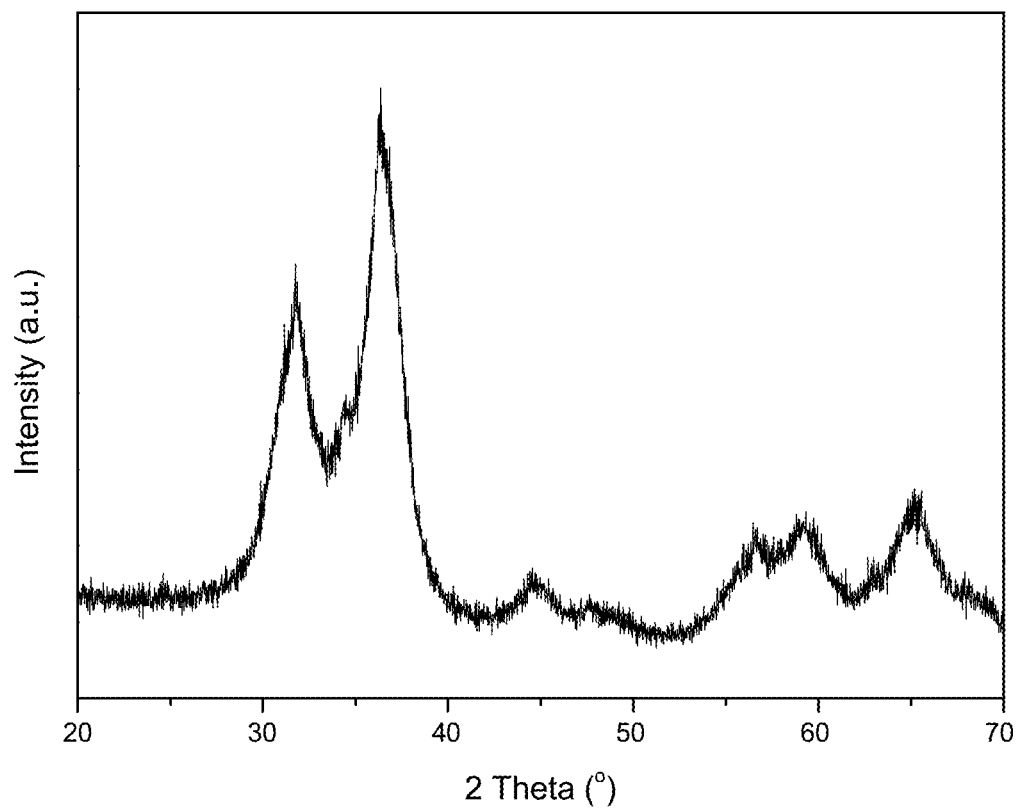
FIG. 1 shows a XRD pattern of material A according to Example 1 of the present application.
Figure 2:
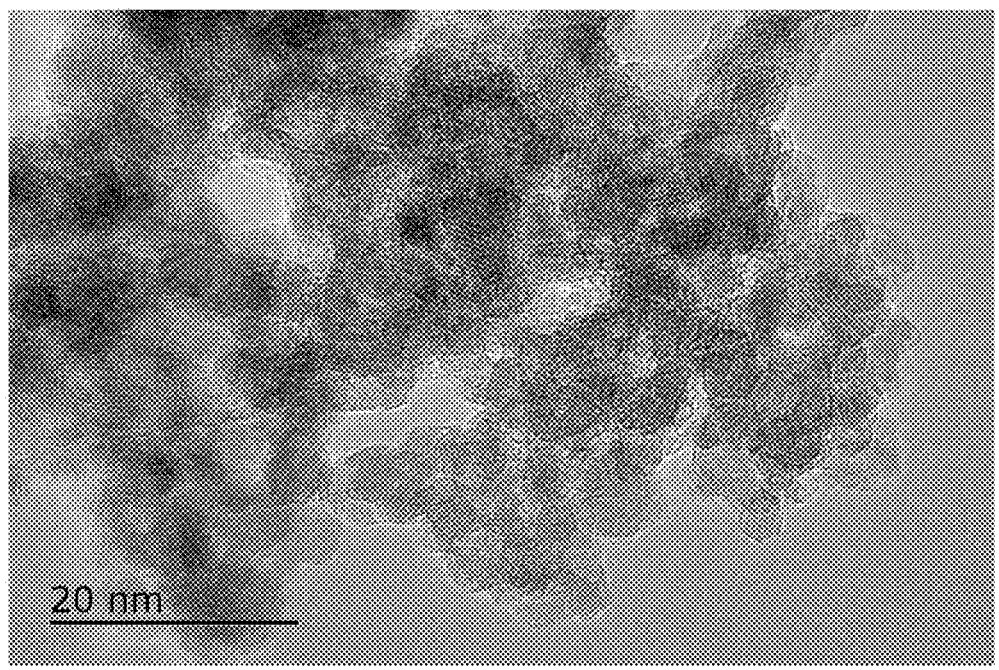
FIG. 2 shows a TEM image of material A according to Example 1 of the present application.

95 g $Zn(NO_3)_2 \cdot 6H_2O$ and 80 g $Al(NO_3)_3 \cdot 9H_2O$ were dissolved in 200 ml deionized water to form a salt solution. 25 g ammonium carbonate was dissolved in 200 ml deionized water to form an alkaline solution. The salt solution and the alkaline solution were mixed in co-current manner by two peristaltic pumps respectively and co-precipitated, wherein the precipitation reaction temperature was controlled at 60° C. and the pH was 7.2. Aging step was then performed at 60° C. for 4 hours, followed by filtering, washing, drying at 100° C. for 24 hours, and then calcining at 500° C. for 4 hours to obtain the zinc-aluminum spinel oxide, which was denoted as A. X-ray fluorescence spectroscopy (XRF) shows that Zn/Al (molar ratio) in the A is 1:1, the XRD pattern of the A is shown in FIG. 1, and the TEM image thereof is shown in FIG. 2.

Example 2

48 g $Zn(NO_3)_2 \cdot 6H_2O$ and 80 g $Al(NO_3)_3 \cdot 9H_2O$ were dissolved in 200 ml deionized water to form a salt solution. 25 g aqueous ammonia (comprising 25% $NH_3$) was dissolved in 200 ml deionized water to form an alkaline solution. The salt solution and the alkaline solution were mixed in co-current manner by two peristaltic pumps respectively and co-precipitated, wherein the precipitation reaction temperature was controlled at 70° C. and the pH was 7.5. Aging step was then performed at 70° C. for 6 hours, followed by filtering, washing, drying at 100° C. for 24 hours, and then calcining at 500° C. for 4 hours to obtain the zinc-aluminum spinel oxide, which was denoted as B. XRF shows that Zn/Al (molar ratio) in the B is 1:2.

Example 3

10.6 g $Zn(NO_3)_2 \cdot 6H_2O$ and 80 g $Al(NO_3)_3 \cdot 9H_2O$ were dissolved in 200 ml deionized water to form a salt solution. 25 g sodium carbonate was dissolved in 200 ml deionized water to form an alkaline solution. The salt solution and the alkaline solution were mixed in co-current manner by two peristaltic pumps respectively and co-precipitated, wherein the precipitation reaction temperature was controlled at 80° C. and the pH was 7.8. Aging step was then performed at 80° C. for 6 hours, followed by filtering, washing, drying at 100° C. for 24 hours, and then calcining at 500° C. for 6 hours to obtain the zinc-aluminum spinel oxide, which was denoted as C. XRF shows that Zn/Al (molar ratio) in the C is 1:9.

Example 4

10.6 g $Zn(NO_3)_2 \cdot 6H_2O$ and 40 g $Al(NO_3)_3 \cdot 9H_2O$ were dissolved in 200 ml deionized water to form a salt solution. 15 g potassium carbonate was dissolved in 200 ml deionized water to form an alkaline solution. The salt solution and the alkaline solution were mixed in co-current manner by two peristaltic pumps respectively and co-precipitated, wherein the precipitation reaction temperature was controlled at 70° C. and the pH was 7.1. Aging step was then performed at 70° C. for 6 hours, followed by filtering, washing, drying at 100° C. for 24 hours, and then calcining at 500° C. for 4 hours to obtain the zinc-aluminum spinel oxide, which was denoted as D. XRF shows that Zn/Al (molar ratio) in the D is 1:4.5.

Example 5

7.7 g $Cr(NO_3)_3 \cdot 9H_2O$ was dissolved in 15 ml deionized water, and then was impregnated with 20 g catalyst B at room temperature for 24 hours, followed by drying at 100° C. for 24 hours, and calcining at 500° C. for 4 hours to obtain 5% (mass fraction) chromium-modified zinc-aluminum spinel oxide, which was denoted as E.

Example 6

4.7 g $Zr(NO_3)_3 \cdot 5H_2O$ was dissolved in 15 ml deionized water, and then was impregnated with 20 g catalyst B at room temperature for 24 hours, followed by drying at 100° C. for 24 hours, and calcining at 500° C. for 4 hours to obtain 5% (mass fraction) zirconium-modified zinc-aluminum spinel oxide, which was denoted as F.

Performance Evaluation of Catalyst

Example 7

The catalyst A was crushed and sieved into particles ranging from 0.4 to 0.8 mm. 2 g obtained particles was loaded into a stainless-steel reaction tube with an inner diameter of 8 mm, and activated with 50 ml/min hydrogen at 300° C. for 1 hour. The reaction was carried out under the following conditions: reaction temperature (T)=320° C., reaction pressure (P)=4.0 MPa, the molar ratio of hydrogen to carbon monoxide in syngas ($H_2$:CO)=3:1, the volume hourly space velocity (GHSV) of the syngas under standard conditions=6000 $h^{-1}$. After reaction for 500 hours, the product was analyzed by gas chromatography. The reaction results are shown in Table 1.

Examples 8 to 12

The reaction conditions and reaction results are shown in Table 1. Other procedures are the same as those in Example 7.

Example 13

The catalyst G was crushed and sieved into particles ranging from 0.4 to 0.8 mm. 2 g obtained particles was loaded into a stainless-steel reaction tube with an inner diameter of 8 mm, and activated with 50 ml/min hydrogen at 300° C. for 1 hour. The reaction was carried out under the following conditions: reaction temperature (T)=320° C., reaction pressure (P)=4.0 MPa, the molar ratio of hydrogen, carbon monoxide and carbon dioxide in syngas ($H_2$:CO:

$CO_2$)=3:1:0.04 (that is, the content of $CO_2$ in the syngas is 1%), the volume hourly space velocity (GHSV) of the syngas under standard conditions=6000 $h^{-1}$. After reaction for 500 hours, the product was analyzed by gas chromatography. The reaction results are shown in Table 1.

Example 14

The catalyst G was crushed and sieved into particles ranging from 0.4 to 0.8 mm. 2 g obtained particles was loaded into a stainless-steel reaction tube with an inner diameter of 8 mm, and activated with 50 ml/min hydrogen at 300° C. for 1 hour. The reaction was carried out under the following conditions: the reaction temperature (T)=320° C., the reaction pressure (P)=4.0 MPa, the molar ratio of hydrogen, carbon monoxide and carbon dioxide in syngas ($H_2$:CO:$CO_2$)=3:1:0.2 (that is, the content of $CO_2$ in the syngas is 4.8%), the volume hourly space velocity (GHSV) of the syngas under standard conditions=6000 $h^{-1}$. After reaction for 500 hours, the product was analyzed by gas chromatography. The reaction results are shown in Table 1.

Example 15

The catalyst G was crushed and sieved into particles ranging from 0.4 to 0.8 mm. 2 g obtained particles was loaded into a stainless-steel reaction tube with an inner diameter of 8 mm, and activated with 50 ml/min hydrogen at 300° C. for 1 hour. The reaction was carried out under the following conditions: the reaction temperature (T)=320° C., the reaction pressure (P)=4.0 MPa, the molar ratio of hydrogen, carbon monoxide and carbon dioxide in syngas ($H_2$:CO:$CO_2$)=3:1:1 (that is, the content of $CO_2$ in the syngas is 20%), the volume hourly space velocity (GHSV) of the syngas under standard conditions=6000 $h^{-1}$. After reaction for 500 hours, the product was analyzed by gas chromatography. The reaction results are shown in Table 1.

TABLE 1

Catalytic Reaction results in Examples 7 to 15

| Example | Catalyst | Reaction condition | CO Conversion efficiency (%) | Dimethyl ether Selectivity (%) | Methanol Selectivity (%) | Hydrocarbons selectivity (%) | $CO_2$ selectivity (%) |
|---|---|---|---|---|---|---|---|
| 7 | A | T = 320° C.; P = 4.0 MPa; GHSV = 6000 $h^{-1}$; $H_2$:CO = 3:1 | 18.2 | 87.6 | 12.3 | 0.1 | 31.4 |
| 8 | B | T = 360° C.; P = 6.0 MPa; GHSV = 10,000 $h^{-1}$; $H_2$:CO = 5:1 | 25.7 | 90.3 | 9.5 | 0.2 | 28.7 |
| 9 | C | T = 370° C.; P = 2.0 MPa; GHSV = 3000 $h^{-1}$; $H_2$:CO = 6:1 | 28.9 | 88.5 | 11.2 | 0.3 | 29.0 |
| 10 | D | T = 400° C.; P = 8.0 MPa; GHSV = 15000 $h^{-1}$; $H_2$:CO = 2:1 | 17.5 | 82.4 | 17.2 | 0.4 | 35.7 |
| 11 | E | T = 300° C.; P = 0.5 MPa; GHSV = 1000 $h^{-1}$; $H_2$:CO = 9:1 | 16.8 | 80.6 | 19.3 | 0.1 | 22.9 |
| 12 | F | T = 450° C.; P = 10.0 MPa; GHSV = 20,000 $h^{-1}$; $H_2$:CO = 1:9 | 2.1 | 82.4 | 17.3 | 0.3 | 20.0 |
| 13 | A | T = 320° C.; P = 4.0 MPa; GHSV = 6000 $h^{-1}$; $H_2$:CO:$CO_2$ = 3:1:0.04 | 17.2 | 86.5 | 13.4 | 0.1 | 23.1 |
| 14 | A | T = 320° C.; P = 4.0 MPa; GHSV = 6000 $h^{-1}$; $H_2$:CO:$CO_2$ = 3:1:0.2 | 10.3 | 84.4 | 15.5 | 0.1 | 14.2 |
| 15 | A | T = 320° C.; P = 4.0 MPa; GHSV = 6000 $h^{-1}$; $H_2$:CO:$CO_2$ = 3:1:1 | 8.8 | 83.5 | 16.4 | 0.1 | 3.2 |

Performance Evaluation of Regenerated Catalyst

Example 16

The deactivated catalyst in Example 7 was treated with a mixture of 2% oxygen and 98% nitrogen in volume fraction at 550° C. for 10 hours to make the catalyst regenerate one round and catalyze reaction under the reaction conditions of Example 7. Five rounds of regeneration were performed in the same way, and the catalytic activity data after reaction for 500 hours in each round were selected for comparison. The results are shown in Table 2.

TABLE 2

Catalytic Reaction results in Example 16

| Regeneration round number | CO Conversion efficiency (%) | Dimethyl ether Selectivity (%) | Methanol Selectivity (%) | Hydrocarbons selectivity (%) | $CO_2$ selectivity (%) | Life per round (h) |
|---|---|---|---|---|---|---|
| 1 | 17.9 | 88.6 | 11.3 | 0.1 | 31.0 | 8500 |
| 2 | 17.6 | 88.0 | 11.9 | 0.1 | 30.9 | 8700 |
| 3 | 17.7 | 87.3 | 12.6 | 0.1 | 30.0 | 8400 |
| 4 | 17.3 | 84.5 | 15.4 | 0.1 | 29.8 | 8500 |
| 5 | 16.9 | 83.8 | 16.1 | 0.1 | 29.7 | 8600 |

The aforesaid only show several examples of the present invention, and do not intend to limit the present invention in any manner. Though relatively preferred examples above disclose the present invention, they do not intend to limit the present invention. Without departing the scope of the technical solutions of the present invention, some variations or modifications made by the skilled in the art, who is familiar with this field by use of the above disclosed technical solutions, are all equal to the equivalent embodiments of the present invention, and fall within the scope of the technical solutions of the present invention.

The invention claimed is:

1. A method for directly preparing dimethyl ether from syngas comprising:
   a) passing syngas through a reaction zone loaded with catalyst, and reacting under a reaction condition sufficient to convert at least part of the syngas as raw materials to obtain a reaction effluent containing dimethyl ether; and
   b) separating dimethyl ether from the reaction effluent;
   wherein, the catalyst is only zinc-aluminum spinel oxide;
   wherein the Zn/Al molar ratio in the zinc-aluminum spinel oxide is Zn/Al=1:9 to 1:1.

2. The method as claimed in claim 1, wherein, the zinc-aluminum spinel oxide is prepared by following steps: formulating a zinc salt and an aluminum salt into a mixed metal salt aqueous solution; contacting the mixed metal salt aqueous solution with a precipitant aqueous solution so as to make the metal ions in the mixed metal salt aqueous solution be co-precipitated followed by aging; washing the obtained precipitate followed by drying and then calcining to obtain the zinc-aluminum spinel oxide.

3. The method as claimed in claim 2, wherein, the method has at least one of the following characteristics:
   the zinc salt and aluminum salt are selected from hydrochloride, sulfate and nitrate;
   the precipitant is selected from sodium carbonate, potassium carbonate, ammonium carbonate, sodium bicarbonate, potassium bicarbonate, ammonium bicarbonate, aqueous ammonia, sodium hydroxide, potassium hydroxide, and mixtures thereof;
   co-precipitation is carried out at a temperature ranging from 20° C. to 95° C.;
   pH during the co-precipitation ranges from 7.0 to 9.0;
   an aging time is not less than one hour; and
   calcination is carried out at a temperature ranging from 450° C. to 800° C.

4. The method as claimed in claim 1, wherein, the zinc-aluminum spinel oxide comprises at least one other element selected from chromium, zirconium, copper, manganese, indium, gallium, and silicon, and a mass fraction of the at least one other element in the zinc-aluminum spinel oxide is less than or equal to 10%.

5. The method as claimed in claim 4, wherein, the at least one other element is added to the zinc-aluminum spinel oxide by impregnating and/or co-precipitating a salt solution of the at least one other element.

6. The method as claimed in claim 5, wherein, the salt of the at least one other element is selected from hydrochloride, sulfate and nitrate.

7. The method as claimed in claim 1, wherein, the reaction zone contains one fixed bed reactor, or multiple fixed bed reactors connected in series and/or in parallel.

8. The method as claimed in claim 1, wherein, the reaction condition comprises: a reaction temperature ranging from 300 to 450° C., a reaction pressure ranging from 0.5 to 10.0 MPa, a molar ratio of hydrogen to carbon monoxide in the syngas ranging from 1:9 to 9:1, and the volume hourly space velocity of syngas under standard conditions ranging from 1,000 to 20,000 $h^{-1}$.

9. The method as claimed in claim 8, wherein, the reaction condition comprises: a reaction temperature ranging from 310 to 360° C., a reaction pressure ranging from 1.0 to 4.0 MPa, a molar ratio of hydrogen to carbon monoxide in the syngas ranging from 3:1 to 6:1, and the volume hourly space velocity of syngas under standard conditions ranging from 3000 to 8000 $h^{-1}$.

10. The method as claimed in claim 1, wherein, the syngas comprises carbon dioxide, and the molar concentration of carbon dioxide in the syngas ranges from 1.0% to 20.0%.

* * * * *